United States Patent [19]

Blanco et al.

[11] 4,029,817

[45] June 14, 1977

[54] SOFT CONTACT LENS PRESERVING SOLUTIONS

[75] Inventors: Milagros V. Blanco, Villa Park; David L. Maurer, Orange, both of Calif.

[73] Assignee: Allergan Pharmaceuticals, Irvine, Calif.

[22] Filed: May 22, 1975

[21] Appl. No.: 580,034

Related U.S. Application Data

[63] Continuation-in-part of Ser. No. 399,692, Sept. 24, 1973, abandoned.

[52] U.S. Cl. .............................. 424/329; 424/80; 424/81; 424/362
[51] Int. Cl.² ...................................... A61K 31/14
[58] Field of Search .............. 424/329, 80, 81, 362, 424/344

[56] References Cited

UNITED STATES PATENTS

| | | |
|---|---|---|
| 3,549,747 | 12/1970 | Krezanoski et al. ................ 424/78 |
| 3,689,673 | 9/1972 | Phares .............................. 424/326 |
| 3,888,782 | 6/1975 | Boghosian et al. ................ 252/106 |

OTHER PUBLICATIONS

McCutcheon's Detergents & Emulsifiers, p. 109 (1972).

Primary Examiner—Leonard Schenkman
Attorney, Agent, or Firm—Martin A. Voet

[57] ABSTRACT

A composition useful in sterilizing soft contact lenses comprising an effective non-toxic amount of a quaternary ammonium compound, such as alkyl (tallow) triethanol ammonium chloride, and an effective detoxifying amount of a polymer such as water soluble polyhydroxyethyl methacrylate, sodium carboxymethyl cellulose, polyoxyethylene sorbitan fatty acid esters such as Polysorbate 80, polyvinyl pyrrolidone, polyoxyethylene alcohols such as polyoxyethylene (20) cetyl ether and mixtures thereof.

6 Claims, No Drawings

SOFT CONTACT LENS PRESERVING SOLUTIONS

REFERENCE TO EARLIER APPLICATION

This application is a Continuation-In-Part of U.S. Ser. No. 399,692 filed Sept. 24, 1973, now abandoned.

BACKGROUND OF THE INVENTION

1. Field of the Invention

The present invention relates to a composition and method for treating contact lenses. More particularly, the present invention relates to a composition and method for soaking and sterilizing soft contact lenses.

2. Background of the Prior Art

Hydrophilic or partially hydrophilic plastic materials have been described for use in making so-called soft contact lenses. For example, U.S. Pat. No. 3,503,393 to Seiderman and U.S. Pat. No. 2,976,576 to Wichterle describes processes for producing three-dimensional hydrophilic polymers of polyhydroxyethylmethacrylate in aqueous reaction media having a sparingly cross-linked polymeric hydrogel structure and having the appearance of elastic, soft, transparent hydrogels. Other soft contact lenses include lenses made out of silicone and other optically suitable flexible materials.

The main virtues of these lenses is their softness and optical suitability. The hydrophilic lenses are particularly useful in ophthalmology due to their remarkable ability to absorb water with a concomitant swelling to a soft mass of extremely good mechanical strength, complete transparency and the ability to retain shape and dimensions when equilibrated in a given fluid.

One of the problems connected with these soft contact lenses is the method of their sterilization and cleaning. The very property of the hydrophilic soft lenses which allows them to absorb up to 150 percent by weight of water also allows preservatives which might otherwise be used for cleaning and sterilization to be absorbed and even concentrated and later released when the soft contact lens is on the eye. The release may be much slower than the uptake, thereby allowing the preservative to build up in the lenses. This build-up eventually effects the physical characteristics of the lenses including dimension, color, etc. This can have the harmful result of damaging or staining the contact lens itself and/or harming the sensitive tissues of the conjunctivae or cornea.

Hard contact lenses do not absorb appreciable amounts of water (i.e. 0.1–0.4%) and thus the use of effective preservatives does not create a problem in the hard contact lens field. However, as stated in U.S. Pat. No. 3,689,673, sterilization of hydrophilic soft contact lenses may be carried out by first soaking in hydrogen peroxide, then sodium bicarbonate and finally normal saline, all at room temperature or by boiling the lenses in normal saline. Furthermore, users of soft contact lenses are warned that under to circumstances should solutions designed for hard contact lenses be used, for the reason that the preservatives in such solutions will be absorbed and even concentrated by the soft lens and may seriously damage the soft lens and/or the eye of the user.

U.S. Pat. No. 3,689,673 further discloses a process of soaking and sterilizing hydrophilic soft contact lenses. Therein it is disclosed that a number of commonly used antimicrobial agents are concentrated in the soft lens. The patent also suggests that these materials may cause corneal damage and that similar in vitro and in vivo tests have shown the undesirability of such antimicrobial agents when used with hydrophilic lenses.

A quaternary ammonium compound having the formula

wherein R is tallow is available from the Miranol Chemical Company under the tradename MIRAMINE TA-30. This compound may be described chemically as a quaternary ammonium compound and has been described as a hair and skin conditioner.

Quaternary amines, e.g. benzalkonium chloride (BAK), are generally known to be bactericidal and are non-toxic to the eye at levels below about 0.01%. As a result, BAK is a commonly used preservative in ophthalmic preparations and hard contact lens care products. However, the same levels of BAK are toxic to the eye when used with soft contact lens because of the tendency of BAK and other quaternary amines to concentrate in the soft lens.

It would therefore be desirable to discover a sterilizing solution for soft contact lenses which does not concentrate in the soft lens, which is non-toxic to the eye and which does not damage or discolor or change the shape of the soft lens.

SUMMARY OF THE INVENTION

It has now been unexpectedly discovered that soft contact lenses may be effectively sterilized and used without damage to the lenses or injury to the eyes of the user by the method of the present invention which comprises contacting the soft lens with a sterile, aqueous, substantially isotonic solution containing as an active ingredient, an effective amount of a quaternary ammonium compound having the structural formula

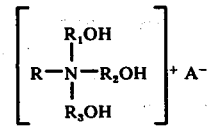

wherein R represents saturated or unsaturated alkyl residues of fatty acids and mixtures thereof containing from about 12–18 carbon atoms and preferably tallow, A is a non-toxic anion and $R_1$, $R_2$ and $R_3$ are the same or different and represent alkyl radicals having 1–3 carbon atoms; and together with a detoxifying amount of a non-toxic compound selected from the group consisting of water soluble polyhydroxyethyl methacrylate, carboxymethyl cellulose, polyoxyethylene sorbitan fatty acid esters, polyoxyethylene alcohols, polyvinylpyrrolidone and mixtures thereof, for a period of time sufficient to sterilize the lens.

The present invention also relates to a sterile, aqueous, substantially isotonic cleaning and sterilizing solution for soft contact lenses comprising the above-described solution.

DESCRIPTION OF THE INVENTION

As discussed above, quanternary ammonium compounds are known to be excellent ophthalmic bactericidal agents, but they are also known to be toxic to the eye when used with soft contact lenses. These facts are confirmed in the Examples below. However, we have now discovered that a number of specific compounds act to prevent the toxic effects of one quaternary ammonium compound without substantial loss of its bactericidal properties. The quaternary ammonium compound which we have discovered how to de-toxify may be decribed by the following formula

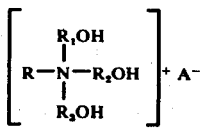

R represents saturated or unsaturated alkyl residues of fatty acids and mixtures thereof containing from about 12–18 carbon atoms. Typical fatty acids include one or more of oleic acid ($C_{17}H_{33}CCOH$), stearic acid ($C_{17}H_{35}COOH$), myristic acid ($C_{13}H_{27}$), palmitic acid ($C_{15}H_{31}COOH$), and linoleic acid ($C_{17}H_{31}COOH$). For reasons of economy, mixtures of these fatty acids derived from natural sources are generally employed rather than pure fatty acids. In a preferred formulation, R is tallow, that is, a naturally occuring mixture of animal fats containing as its primary constituents, stearic acid, palmitic acid and oleic acid.

The foregoing definition of R is consistent with the accepted definitions of quaternary ammonium compounds, e.g. 1975 United States Pharmacopeia definitions for conventional quaternary ammonium compounds, e.g. page 552 benzalkonium chloride. A represents any conventional, non-toxic anion residue such as, for example, Cl, $NO_3$, $SO_4$, etc. $R_1$, $R_2$ and $R_3$ are the same or different and represent alkyl groups 1–3 carbon atoms and preferably $R_1=R_2=R_3=$ethyl.

The preferred compound is alkyl (tallow) triethanol ammonium chloride and is available commercially. The compound is fairly stable in acidic pH but tends to precipitate out of solution as the base under alkaline conditions.

The amount of the foregoing active ingredient which may be used in the present invention ranges from about 0.01 to about 0.1 percent (w/v) and preferably from about 0.03 to about 0.06 percent (w/v).

The compounds which act to detoxify the active ingredient, yet allow the active ingredient to retain its bactericidal properties, are one or more of the following detoxifying componds: water soluble polyhydroxyethyl methacrylate, carboxymethyl cellulose, polyoxyethylene sorbitan fatty acid esters, polyoxyethylene alcohols and polyvinylpyrrolidone. The preferred compounds are the water soluble polyhydroxyethyl methacrylate, sodium carboxymethyl cellulose, polyoxyethylene (20) sorbitan monooleate or Polysorbate 80 ("Tween 80") and polyoxyethylene (20) cetyl ether ("Brij 58").

The water soluble polyhydroxyethyl methacrylate described herein is soluble in alkaline water, the solubility varying with the alkalinity of the water and also on the degree of polymerization. The preferred grade is the polymer with an average molecular weight of about 60,000 to 700,000 preferably having an average molecular weight of about 80,000 to 225,000. These polymers are available from Hydron Laboratories, e.g. under the trademark "Hydron Biomedical Polymer, Type Al".

Carboxymethylcellulose or sodium carboxymethylcellulose is a synthetic cellulose gum containing 0.4 to 1.5 sodium carboxymethyl groups ($-CH_2COONa$) per glucose unit of the cellulose. It is a white, odorless, non-toxic hygroscopic powder readily dispersible in hot or cold water. The pH of a 1% solution is 6.5–8.0.

The polyoxyethylene sorbitan fatty acid esters, i.e. the "Tween" series of surfactants, are exemplified by Polysorbate 80. The Polyoxyethylene alcohols, i.e. the "Brij" series of surfactants, are exemplified by "Brij 58". Polysorbate 80, otherwise described as polyoxyethylene (20) sorbitan monooleate, is an oleate ester of sorbitol and its anhydrides copolymerized with approximately 20 moles of ethylene oxide for each mole of sorbitol and sorbitol anhydrides. Polysorbate 80 is available commercially from Atlas Chemical Company under the name "Tween 80". "Brij 58", also a tradename of Atlas Chemical Company, is polyoxyethylene (20) cetyl ether. The other well known members of the "Tween" and "Brij" series of surfactants may also be used in the present invention.

The amount of the detoxifying compounds which may be used in the present invention varies from about 0.01 to about 2.0 and preferably from about 0.04 to about 0.4 percent by weight.

The detoxifying compounds described herein also have been found to minimize the accumulation of deposits on the surface of the soft contact lenses. The manner in which these compounds inhibit the formation of the deposits on the surface of the soft contact lenses is not known. However, it has been hypothesized that positively charged proteinaceous materials which would otherwise react with the soft contact lens react instead with the detoxifying compounds and thereby prevent the deposits from forming on the lenses.

A typical composition of the present invention may contain, in addition to the active ingredients described earlier, buffers, stabilizers and isotonic agents which aid in making the opthalmic cleaning composition more comfortable to the user. These additional materials must be non-toxic and must not distort the soft lens. In this regard, we have found the Polysorbate 80 and Brij 58 also act to stabilize the aqueous formation in amounts ranging from about 0.05 to about 0.6 and preferable about 0.2% (w/v).

Suitable buffers include sodium or potassium citrate, citric acid, boric acid, various mixed phosphate buffers including combinations of $Na_2HPO_4$, $NaH_2PO_4$, $KH_2PO_4$ and $NaHCO_3$. Generally, buffers may be used in amounts ranging from about 0.05 to 2.5 and preferably 0.1 to 1.5% (w/v).

The treating solution for soft contact lenses should be maintained at an osmotic pressure similar to that of physiologic saline, i.e. substantially isotonic, or approximately 0.9% saline, or with suitable agents alone or in combination to render the solution substantially isotonic. Hypotonic solution, e.g., tap water, will cause the lens to adhere tightly to the cornea while hypertonic solutions (excess saline) will result in stinging, lacrimation and a red eye.

A preferred formulation for use in the present invention is the following aqueous composition comprising the following compounds at approximately the indicated concentrations:

| | % |
|---|---|
| Alkyl (tallow) triethanol ammonium chloride | 0.03 |
| Polyhydroxyethylmethacrylate | 0.04 |
| Polyoxyethylene (20) sorbitan monooleate | 0.20 |
| Propylene glycol | 1.50 |
| Sodium bicarbonate | 0.204 |
| Sodium phosphate, dibasic, anhydrous | 0.20 |

| | % |
|---|---|
| Sodium phosphate, monobasic, monohydrate | 0.09 |
| Sodium thimerosal | 0.002 |

The above-described components of the present invention are non-toxic and are capable of being sterilized without change in composition. Additionally, these components are safe for ophthalmic use with conventional hard contact lenses as well as the "soft'-'contact lenses.

It should be understood that the foregoing description of the amounts of the various compounds which may be used in the present invention are stated in percentage of ingredients in solution. The formulation may also take the form of one or more conventional solid dosage forms such as tablets suitable for use in a measured quantity of a suitable solvent such as water. The percentage composition of the solid dosage forms is such that when dissolved in a specified volume of water, the solution will have the percentage composition within the ranges set forth in the specification. If solid dosage forms are used, the formulation may include conventional lubricants, binders, and excipients which include glycerol, sorbitol, boric acid, propylene glycol, polyethylene glycols, dextran and methylcellulose. These materials are used in amounts varying between 0.01 and 10 and preferably between about 0.1 and 5 weight percent.

The method of use of the sterilizing and cleaning solution is the following. The lenses are first rinsed with a few drops of the subject solution to remove contaminants such as mucous, eye makeup etc., and then placed in a suitable container with sufficient amount of the subject solution to cover the lenses. The lenses are allowed to soak for at least about 30 minutes and preferably 2 to 8 hours to achieve 99.9% kill of spores, fungi and yeasts. This soaking has been shown to effectively clean and sterilize the lenses and inhibit the formation of proteinaceous deposits on the lenses. The foregoing method is carried out at ambient temperature or elevated temperatures, i.e., about 40°–100° C.

The word "sterilize" is used in the present invention to mean the rendering non-viable of substantially all pathogenic bacteria of the type typically found, including Gram negative and Gram positive bacteria as well as fungi, except as indicated.

Effective amounts of non-toxic agents suitable for use in substantially sterilizing or preserving soft contact lenses may also be used in combination with the present invention. Examples of non-toxic agents include suitable amounts of water soluble, e.g. Na and K, salts of compounds, such as, for example, sodium thimerosal, disodium edetate and mixtures thereof. Sodium thimerosal may be used in amounts which are non-toxic and which are effective at concentrations varying from about 0.001 to about 0.01 percent and preferably 0.001–0.005 percent. Disodium edetate may be used in amounts which are non-toxic and which are effective at concentrations ranging from about 0.001 to about 0.01 percent and preferably 0.05%.

To illustrate the manner in which the invention may be carried out, the following examples are given. It is understood, however, that the examples are for the purposes of illustration and the invention is not to be regarded as limited to any of the specific materials or conditions set forth therein. Unless other wise stated, "%" means (w/v).

EXAMPLE I

Several experiments were performed to determine the toxicity of benzalkonium chloride (BAK) in connection with soft contact lenses when used alone and when used in the presence of a detoxifying polymer of the type disclosed herein. The content of each numbered solution is shown in Table 1.

Experiment No. 1 — Toxicity of BAK used without detoxifying polymers

Twenty-four hours prior to the onset of the study, the experimental and control eyes of an adult female albino New Zealand rabbit were stained with one drop of 2 percent fluorescein for observation under U.V. light to ensure normal corneas. This procedure was again adhered to at the conclusion of the study. the scoring of the ocular reactions was based on the method described in "Appraisal of the Safety of Chemicals in Foods, Drugs and Cosmetics", 1965, page 51.

One unused Bausch & Lomb soft contact lens was soaked overnight in 5.0 cc of Solution No. 1 (0.004% BAK). In the morning, it was fitted in the left eye of one adult rabbit for approximately 6 hours' wearing time. The animal was observed regularly for possible lens rejection and irritation of the eye muscosa. The results of the study were as follows:

a. Comfort: Mild discomfot upon fitting of the soft lens characterized by repeated blinking and squinting for approximately 4 minutes.

b. Mucosal Irritation: Mild hyperemia, moderate chemosis and discharge present upon removal of lens.

c. Toxicity: Severe corneal erosion over entire area covered by the lens.

d. Conclusion: Solution No. 1 (0.004% BAK) is extremely toxic in the presence of a soft contact lens.

Experiment No. 2 — Toxicity of several concentrations of BAK in the presence of a detoxifying polymer A. The procedure of Experiment No. 1 was followed, except Solution No. 3 was used instead of Solution No. 1.

1. Comfort: Acceptable.
2. Mucosal Irritation: A very mild transient conjunctival irritation was present.
3. Toxicity: Concentrated stippling in the lower portion of the cornea.

B. Experiment 2A. was repeated using three rabbits. The results of the study are shown below:

1. Comfort: Acceptable.
2. Mucosal Irritation: A slight conjunctival irritation occurred in all test subjects.
3. Toxicity: None.

Conclusion: On the basis of Experiments 2A and B, it is concluded that Solution No. 3 is not toxic to rabbit eyes in the presence of the Bausch & Lomb soft contact lens.

C. Experiment 2A was repeated, except Solution No. 4 (0.01% BAK) was used instead of Solution No. 3 (0.004% BAK). The following results were obtained:

1. Comfort: Acceptable.
2. Mucosal Irritation: Mild conjunctival irritation increased to moderate with time.
3. Toxicity: Deep stippling surrounded by diffuse haziness over the entire area covered by the lens.

Conclusion: Solution No. 4 is toxic to rabbit eyes in the presence of a soft contact lens.

D. Experiment 2(a) was repeated, except Solution No. 5 (0.03% BAK) was used instead of Solution No. 3. The following results were obtained:
1. Comfort: Acceptable.
2. Mucosal Irritation: Mild conjunctival irritation with moderate chemosis and discharge.
3. Toxicity: Moderate corneal staining over the entire area covered by the lens.

Conclusion: Solution No. 5 is toxic to rabbit eyes in the presence of a soft contact lens.

In experiments 1 and 2 in Example I, the toxicity of a typical quaternary ammonium compound, benzalkonium chloride (BAK), was tested both with and without the subject detoxifying polymers.

Experiment No. 1 shows that a low concentration, i.e., 0.004% solution of BAK is toxic when used with soft contact lenses.

Experiment No. 2 shows the toxicity of BAK solutions when used in combination with detoxifying polymers. BAK concentrations of 0.004%, 0.01% and 0.03% were tested. Both of the higher concentrations of BAK were toxic nonetheless. The lowest concentration of BAK (0.004%) was determined to be not toxic, although one of 4 rabbits tested exhibited some corneal damage.

EXAMPLE II

Several experiments were preformed to determine the anti-microbial activity of BAK alone and in the presence of detoxifying polymers of the type disclosed herein. The content of each numbered solution is shown in Table 1.

Experiment No. 3 — Antimicrobial activity of Solution No. 2 — (0.004% BAK alone)

Solution No. 2 was tested on the indicated microorganisms. 10 ml aliquots of solution were inoculated to contain approximately $10^5$ cells/ml. After 6 hours' contact time, the remaining number of viable cells was quantitated by 10 fold dilutions in broth media and plated on spread agar plates. The results are shown below in Table 1.

Table 1

| Microorganisms | Control | Test Formulation |
|---|---|---|
| S. aureus | $1 \times 10^5$ (+++) | $<10^2$ (000) |
| C. albicans | $2 \times 10^6$ (+++) | $<10^2$ (000) |
| A. niger | $1 \times 10^5$ (+++) | $<10^2$ (000) |
| S. marcescens | $9 \times 10^5$ (+++) | $<10^2$ (000) |

Conclusion: Solution No. 2 showed good reduction of all microorganisms tested. That is, all microorganisms were reduced to less than $10^2$ and all tube dilutions were negative.

Experiment No. 4 — Antimicrobial tests of Solutions No. 3, 4, 5 containing BAK and detoxifying polymers The procedure of Experiment 3 was followed, except Solutions No. 3, 4 and 5 were tested instead of Solution No. 2 with the indicated organisms. The results are shown in Table 2 below.

Table 2

|  | Control | Solution No. 3 | Solution No. 4 | Solution No. 5 |
|---|---|---|---|---|
| S. marcescens | $8 \times 10^5$ | $<10^2$ (000) | $<10^2$ (000) | $<10^2$ (000) |
| S. aureus | $3 \times 10^5$ | $<10^2$ (000) | $<10^2$ (000) | $<10^2$ (000) |
| P. aeruginosa | $4 \times 10^5$ | $<10^2$ (000) | $<10^2$ (000) | $<10^2$ (000) |
| E. coli | $3 \times 10^5$ | $<10^2$ (000) | $<10^2$ (000) | $<10^2$ (000) |
| C. albicans | $5 \times 10^5$ | $1 \times 10^4$ (+++) | $5 \times 10^3$ (+++) | $6 \times 10^2$ (+++) |
| A. niger | $3 \times 10^5$ | $3 \times 10^3$ (0++) | $1 \times 10^2$ (0++) | $2 \times 10^4$ (0++) |

Conclusion: Each of Solutions 3, 4 and 5 has good activity against the first four organisms, but they do not satisfactorily inhibit the latter two organisms. Failure to inhibit the latter two organisms renders the solutions bactericidally inadequate for use as a soft contact lens sterilizing solution.

In experiments 3 and 4 in Example II, the antimicrobial spectrum of the solutions previously tested for toxicity in Experiments 1 and 2 were determined.

Experiment No. 3 shows tht 0.004% BAK without the detoxifying polymers has a good antibacterial spectrum. of course, experiment No. 1 showed that this concentration of BAK was toxic.

Experiment No. 4 shows the antimicrobial activity of the BAK-containing solutions tested in Experiment No. 2. None of these solutions had an adequate spectrum of antibacterial activity. The 0.004% BAK solution, the only possibly non-toxic BAK formulation, had the poorest bactericidal spectrum and was unacceptable for use as a sterilizing agent for soft contact lenses.

The foregoing tests demonstrate that BAK is not effectively detoxified by the subject detoxifying polymers except at very low concentrations of BAK and furthermore that the subject detoxifying polymers interfere with BAK's bactericidal spectrum. That is, in combination with the detoxifying polymers, BAK loses a significant amount of its bactericidal properties and is not useful as a sterilizing agent for soft contact lenses.

EXAMPLE III

Several experiments were performed to determine the toxicity of alkyl (tallow) triethanol ammonium chloride alone and in the presence of the following detoxifying polymers: Polysorbate 80, water soluble polyhydroxyethyl methacrylate, sodium carboxymethyl cellulose, polyvinylpyrrolidone, Polyoxyethylene (20) cetyl ether and mixtures thereof. The experiments are shown below:

Experiment No. 5 — Toxicity of alkyl (tallow) triethanol ammonium chloride without detoxifying polymer Six Bausch & Lomb "Soflens" soft contact lenses were soaked 16—17 hours in 10 cc of Solution No. 6 (0.01% alkyl (tallow) triethanol ammonium chloride). The lenses were then fitted into the left eyes of six adult female New Zealand albino rabbits for approximately 3½–4 hours' wearing time. Each lens was assigned to individual rabbits for the duration of the study. The procedure used in Experiment No. 1 was used to determine toxicity.

Observations: No discomfort was noted in any of the rabbits upon fitting the soft lenses. After 90 minutes of wear, the experimental eyes of rabbits tested with solution No. 6 developed a mild conjunctival irritation which 2 hours later appeared moderately inflamed. Mucous discharge was also noted at this time in these animals.

All test subjects with Solution No. 6 exhibited varying degrees of ocular abnormality. Two rabbits were observed with iris folds above normal and marked congestion. Hyperemia of the conjunctivae was evident in five animals with vessels definitely injected above normal; one of these five experienced redness of a more diffuse, deeper crimson, including individual vessels not easily discernible. Chemosis, with swelling above normal, appeared in one test subject. Four rabbits displayed discharge, varying from slight to moderate, with moistening of the lids and hairs just adjacent to the lids. Upon fluorescein staining, all six rabbits exhibited lesions involving ¾ to the whole lens area in the lower ranging half of the cornea, from opalescent areas with details of the iris not visible and size of the pupil barely discernible to an opaque condition with the iris invisible.

Conclusion: This test showed that alkyl (tallow) triethanol ammonium chloride in the absence of detoxifying polymers induced severe corneal damage and pronounced irritation of the conjunctivae in adult rabbits when used with soft contact lenses.

Experiment No. 6 — Toxicity of alkyl (tallow) triethanol ammonium chloride in the presence of detoxifying polymers polyhydroxyethol methacrylate and Polysorbate 80

A. Concentration in the Lens

1. Three sets of three Bausch & Lomb "Soflens" soft contact lenses were soaked in 5.0 ml of Solution No. 7. A solution blank of 5.0 ml was carried through the entire procedure. After 4 days' soaking, the concentration of alkyl triethanol ammonium chloride was determined. The lenses were soaked in the remaining solution for 21 days longer for a total of 25 days and the concentration of alkyl triethanol ammonium chloride was again determined.

2. Three sets of Bausch & Lomb "Soflens" soft contact lenses were soaked in 5.0 ml of Solution No. 7 diluted 1 to 10 with saline. The above test regimen was followed. After 25 days, the lenses were soaked in a fresh dilution of the formulation for 27 hours with shaking. The alkyl triethanol ammonium chloride concentrations in the soaking solutions were then determined.

RESULTS

The results of the tests indicated that the alkyl triethanol ammonium chloride was not concentrated by the soft lens, even after soaking.

B. Lens Stability

The following procedure was followed for the first 90 days of the study. Four Bausch & Lomb "Soflens" soft contact lenses each were soaked separately for 8 hours in 10.0 ml of fresh Solution No. 7 in glass bottles with polyethylene caps, at three different temperature conditions: room temperature, 32° C, and 45° C. This was followed by a 16-hour daily soak in 10 ml of isotonic saline at corresponding temperatures.

After the first 90 days, the procedure was altered slightly. This involved a daily 16-hour soak in Solution No. 7 and an 8-hour soak in isotonic saline following the same procedure for a period of 105 days.

RESULTS

The results indicated that the soft contact lens diameter and water content remained essentially the same during the five and a half months of compatibility studies at each temperature.

c. Rabbit Toxicity

1. Test Method

Each of three unused Bausch & Lomb "Soflens" soft contact lenses was soaked overnight in 5.0 cc of Solution No. 7, and in the morning the lenses were fitted in the left eyes of three adult rabbits for approximately 7 hours' wearing time. Each lens was assigned to an individual rabbit for the duration of the study. Following each day's wear, the lenses were rinsed with normal saline and placed in clean lens bottles containing a fresh amount of soaking solution. The animals were observed regularly for possible lens rejection and irritation of the eye mucosa. On day 16 of the study, nine additional test animals were added to the study. The procedure used with these rabbits was the same as that used with the initial three rabbits.

Some of the test animals were removed from the study because of either damage to or proteinaceous deposits on the lens. At no time during the 211-day test were any of the test animals removed from the study because of toxic reactions. Three rabbits remained on the last day of the study.

TEST RESULTS

No untoward ocular reactions were observed in any of the test subjects following 211 days of testing.

Conclusion: Solution No. 7 is not toxic or irritating to rabbit eyes following 211 consecutive days of testing.

Experiment No. 7 — Toxicity of alkyl (tallow) triethanol ammonium chloride in the presence of detoxifying polymers sodium carboxymethyl cellulose and Polysorbate 80

Experiment No. 6C. was repeated, except Solution No. 9 was tested instead of Solution 7, for 91 days rather than 211 days and with 10 adult female New Zealand albino rabbits rather than three rabbits. The results were as follows:

The test results were the same as Experiment 6C. over the 91 days of the study.

Conclusion: Solution No. 9 is not toxic to rabbit eyes in the presence of soft contact lenses.

Experiment No. 8 — Toxicity of alkyl (tallow) triethanol ammonium chloride in the presence of detoxifying polymers polyvinylpyrrolidone and Polysorbate 80

Experiment No. 6C. was repeated, except Solution No. 8 was used instead of Solution No. 7, for 22 days rather than 211. The test results were the same as Experiment 6C. over the 22 days of the study.

Conclusion: Solution No. 8 is not toxic rabbit eyes in the presence of soft contact lenses.

Experiment No. 9 — Toxicity of alkyl (tallow) triethanol ammonium chloride in the presence of detoxifying polymers polyoxyethylene (20) cetyl ether and polyhydroxyethyl methacrylate Experiment No. 6C. was repeated, except solution No. 10 was used instead of Solution No. 7, for 45 days rather than 211 and with four adult female New Zealand albino rabbits rather than three rabbits. The test results were the same as Experiment 6C. over the 45 days of the study.

Conclusion: Solution No. 10 is not toxic to rabbit eyes in the presence of soft contact lenses. (In a previous test of one batch of Solution No. 10, sporadic corneal lesions were observed. This study confirmed that Solution No. 10 is non-toxic.)

In experiments 5–9 in Example III, the toxicity of alkyl triethanol ammonium chloride was tested both with and without the subject detoxifying polymers.

Experiments 5–9 demonstrate that a 0.03% solution of alkyl (tallow) triethanol ammonium chloride is toxic alone, but can be completely detoxified by one or more of Applicants' detoxifying polymers. The detoxifying polymers used in these experiments are Polysorbate 80, polyhydroxyethyl methacrylate, polyvinylpyrrolidone, polyoxyethylene (20) cetyl ether, sodium carboxymethyl cellulose and mixtures thereof.

EXAMPLE IV

Several experiments were performed to determine the anti-microbial activity of alkyl triethanol ammonium chloride in the presence of detoxifying polymers of the type disclosed herein. The content of each numbered solution is shown in Table 1.

Experiment No. 10 — Antimicrobial Test of Solution No. 7 a. Solution No. 7 was subjected to standardized microbiological studies.

Solution No. 7 was challenged by the following panel of five organisms:
  a. Staphylococcus aureus ATCC No. 6538 (Gram positive)
  b. Pseudomonas aeruginosa ATCC No. 9027 (Gram negative)
  c. Escherichia coli ATCC No. 8739 (Gram negative)
  d. Candida albicans ATCC No. 10231 (yeast-like fungus)
  e. Aspergillus niger ATCC No. 16404 (fungus)

10 ml aliquots of solution No. 7 was inoculated with approximately $5 \times 10^5$ cells/ml. After 6 hours' contact time, the remaining number of viable organisms are quantitated by the same procedure used in Experiment No. 4 herein.

RESULTS

Solution No. 7 reduced a standard panel of five organisms, namely, S. aureus, P. aeruginosa, E. coli, C. albicans, and A. niger to less than $10^2$ microorganisms within a 6-hour contact time. An additional organism, S. marcescens, required 8 hours of contact time.

Solution No. 7 was particularly effective against S. aureus and P. aeruginosa. The contact time required for attaining complete sterility was 30 minutes for S. aureus and less than two hours for P. aeruginosa.

Experiment No. 11 — Antimicrobial test of Solution Nos. 8 and 10

Experiment No. 10 was repeated, except Solutions 8 and 10 were used instead of Solution 7 and the indicated organisms were used. The results are shown below in Table 3:

Table 3

| Microorganisms | Control | Solution No. 8 | Solution No. 10 |
|---|---|---|---|
| S. aureus | $1 \times 10^5$ | $<10^2$ (000) | $<10^2$ (0+0) |
| C. albicans | $1 \times 10^6$ | $<10^2$ (000) | $<10^2$ (+00) |
| A. niger | $3 \times 10^5$ | $<10^2$ (+0+) | $<10^2$ (+++) |
| S. marcescens | $2 \times 10^5$ | $<10^2$ (0+0) | $2 \times 10^2$ (0++) |

Conclusion: Solution No. 8 showed good reduction of all microorganism tested. That is, all microorganisms were reduced to less than $10^2$ and most tube dilutions were negative.

Solution No. 10 is comparable to Solution No. 8 except that A. niger was reduced 2 logs rather than 3 logs.

In experiments 10 and 11 in Example IV, the antimicrobial activity of the claimed non-toxic solutions tested in Example III are determined. In experiments 10 and 11, all solutions tested were shown to have adequate bactericidal activity to be used to sterilize soft contact lenses.

EXAMPLE V

An experiment was conducted to determine the toxicity in the presence of soft contact lenses of a conventional hard contact lens wetting solution.

Experiment No. 12 — Toxicity of conventional hard contact lens wetting solution

A conventional hard contact lens wetting solution was tested for toxicity with soft contact lenses in two adult female albino New Zealand rabbits. The wetting solution contained 0.004% benzalkonium chloride (BAK) in a Liquifilm base (Allergan Pharmaceuticals' brand) consisting of hydroxypropylmethyl cellulose and polyvinyl alcohol in an aqueous, isotonic carrier. The procedure of Experiment No. 5 was used.

RESULTS

After 5 days, corneal lesions were observed in the rabbits.

Conclusion: Conventional BAK-preserved hard contact lens wetting solutions are toxic to rabbit eyes in the presence of soft contact lenses.

Experiment 12 in Example V demonstrates that a conventional hard contact lens wetting solution containing BAK and hydroxypropylmethyl cellulose was toxic to rabbit eyes in the presence to soft contact lenses.

The foregoing Examples show that BAK, even at a concentration as low as 0.004%, is toxic in the presence of soft contact lenses. Further, that at a low concentration (0.004%), BAK can be partially detoxified by the subject detoxifying polymers. However, the microbicidal activity of BAK is also substantially diminished by the detoxifying polymers rendering the partially detoxified composition unfit for use as a soft contact lens sterilizing solution.

The subject active quaternary ammonium compound, alkyl (tallow) triethanol ammonium chloride is toxic in the presence of soft contact lenses without the subject detoxifying polymers. However, the subject active quaternary ammonium compound can be detoxified by the subject polymers without substantial loss of bactericidal activity.

Table 1

| | Solutions (%) | | | | |
|---|---|---|---|---|---|
| | No. 1 | No. 2 | No. 3 | No. 4 | No. 5 |
| Benzalkonium chloride | 0.004 | 0.004 | 0.004 | 0.01 | 0.03 |
| Sodium bicarbonate | 0.08 | 0.05 | 0.204 | 0.20 | 0.204 |
| Sodium thimerosal | 0.0044 | 0.0044 | 0.002 | 0.002 | 0.002 |
| Sodium chloride | 0.9 | 0.9 | — | — | — |
| Propylene glycol | — | — | 1.50 | 1.50 | 1.50 |
| Polysorbate 80 | — | — | 0.20 | 0.20 | 0.20 |
| Disodium phosphate | — | — | 0.20 | 0.20 | 0.20 |
| Sodium phosphate | — | — | 0.09 | 0.09 | 0.09 |
| Polyhydroxyethyl methacrylate | — | — | 0.04 | 0.0044 | 0.04 |
| Purified water | to 100% | to 100% | to 100% | to 100% | to 100% |

| | Solutions (%) | | | | |
|---|---|---|---|---|---|
| | No. 6 | No. 7 | No. 8 | No. 9 | No. 10 |
| Alkyl triethanol ammonium chloride[1] | 0.01 | 0.03 | 0.03 | 0.03 | 0.033 |
| Sodium carboxymethyl cellulose | — | — | — | 0.1 | — |
| Polyhydroxyethyl methacrylate[2] | — | 0.04 | 0.04 | — | 0.04 |
| Polyoxyethylene (20) cetyl ether | — | — | — | — | 0.2 |
| Polysorbate 80 | — | 0.20 | 0.20 | 0.20 | — |
| Polyvinylpyrrolidone[3] | — | — | 1.0 | — | — |
| Propylene glycol | — | 1.50 | 0.55 | 1.50 | 1.5 |
| Sodium bicarbonate | 0.05 | 0.204 | 0.204 | 0.204 | 0.204 |
| NaCl | 0.9 | — | — | — | — |
| Disodium phosphate | — | 0.20 | 0.20 | 0.20 | 0.20 |
| Sodium phosphate | — | 0.09 | 0.09 | 0.09 | 0.09 |
| Sodium lactate | — | — | 0.5 | — | — |
| Sodium thimerosal | — | 0.002 | 0.002 | 0.002 | 0.002 |
| Purified water | to 100% | to 100% | to 100% | to 100% | to 100% |

[1]Alkyl triethanol ammonium chloride: alkyl is tallow ("Miramine TA-30").
[2]Polyhydroxyethyl methacrylate: M.W. between about 60,000 – 700,000.
[3]Polyvinylpyrrolidone: "Plasdone K-29-32."

1) Alkyl triethanol ammonium chloride: alkyl is tallow ("Miramine TA-30"). 2) Polyhydroxyethyl methacrylate: M.W. between about 60,000 - 700,000. 3) Polyvinylpyrrolidone: "Plasdone K-29-32".

We claim:

1. A method of sterilizing soft contact lenses comprising contacting a soft contact lens with an effective amount of a sterile, aqueous, non-toxic composition comprising about 0.01 to about 0.1 percent (w/v) of a quaternary ammonium compound having the formula:

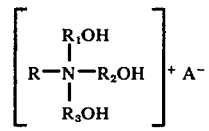

wherein A is a non-toxic anion, R is selected from the group consisting of saturated and unsaturated alkyl residues of fatty acids and mixtures thereof having from about 12–18 carbon atoms, $R_1$, $R_2$ and $R_3$ may be the same or different and are alkyl groups having 1–3 carbon atoms, and from about 0.01 to about 2 percent 2. The method of claim 1 wherein the composition additionally contains about 0.001 to about 0.005 percent (w/v) of sodium thimerosal.

3. The method of claim 1 wherein $R_1$, $R_2$ and $R_3$ are each ethyl groups.

4. The method of claim 1 wherein R is tallow.

5. A method of sterilizing soft contact lenses comprising contacting a soft contact lens with an effective amount of a sterile, aqueous, substantially isotonic non-toxic composition comprising about 0.01 to about 0.1 percent (w/v) of alkyl (tallow) triethanol ammonium chloride, from about 0.01 to about 2 percent (w/v) of water soluble polyhydroxyethyl methacrylate having an average molecular weight of about 60,000 to 700,000, from about 0.01 to about 2 percent (w/v) of polyoxyethylene (20) sorbitan monooleate and about 0.001 to about 0.005 percent (w/v) of sodium thimerosal.

6. A method of sterilizing soft contact lenses comprising contacting a soft contact lens with an effective amount of an aqueous non-toxic composition useful for sterilizing contact lenses comprising the following components at approximately the indicated concentrations:

| | % |
|---|---|
| Alkyl (tallow) triethanol ammonium chloride | 0.03 |
| Polyhydroxyethylmethacrylate | 0.04 |
| Polyoxyethylene (20) sorbitan monooleate | 0.20 |
| Propylene glycol | 1.50 |
| Sodium bicarbonate | 0.204 |
| Sodium phosphate, dibasic, anhydrous | 0.20 |
| Sodium phosphate, monobasic, monohydrate | 0.09 |
| Sodium thimerosal | 0.002 |

* * * * *